United States Patent [19]
Ryan et al.

[11] Patent Number: 5,492,532
[45] Date of Patent: Feb. 20, 1996

[54] BALLOON CATHETER

[75] Inventors: William P. Ryan, Minnetonka; Edward A. Barlow, Bloomington, both of Minn.

[73] Assignee: B. Braun Medical, Inc., Plymouth, Minn.

[21] Appl. No.: 290,139

[22] Filed: Aug. 15, 1994

Related U.S. Application Data

[63] Continuation-in-part of Ser. No. 953,481, Sep. 29, 1992, Pat. No. 5,338,299, which is a continuation-in-part of Ser. No. 871,722, Apr. 21, 1992, Pat. No. 5,171,297, which is a continuation of Ser. No. 324,913, Mar. 17, 1989, Pat. No. 5,112,304.

[51] Int. Cl.$^6$ ............................................... A61M 29/00
[52] U.S. Cl. .................... 604/96; 604/280; 604/283; 606/194; 606/191
[58] Field of Search ............................ 128/657; 604/96, 604/97, 98, 99, 100, 101, 102, 103, 280, 283; 606/191, 192, 194, 195

[56] References Cited

U.S. PATENT DOCUMENTS

| | | | |
|---|---|---|---|
| 4,126,134 | 11/1978 | Bolduc et al. | 604/96 |
| 4,545,367 | 10/1985 | Tucci | 606/195 |
| 5,112,304 | 5/1992 | Barlow et al. | 604/96 |
| 5,114,403 | 5/1992 | Clarke et al. | 604/95 |
| 5,167,239 | 12/1992 | Cohen et al. | |
| 5,171,297 | 12/1992 | Barlow et al. | 604/96 |
| 5,185,004 | 2/1993 | Lashinski | 604/95 |
| 5,338,299 | 8/1994 | Barlow | 604/96 |

Primary Examiner—Corrine M. Maglione
Assistant Examiner—N. Kent Gring
Attorney, Agent, or Firm—Joel D. Skinner, Jr.; Hugh D. Jaeger

[57] ABSTRACT

A balloon consisting of braided fibers encapsulated between two plastic elastomeric materials affixes to a distal end of a catheter. The braided fibers provide reinforcement to contain pressure and determine the maximum diameter of the balloon on expansion. The elastomeric material provides for fluid containment and collapsing of the balloon after pressurization. An embedded spring in an elastomeric material internal to the catheter provides memory to assist in collapsing the balloon after pressurization. The embedded spring extends from the distal end of the catheter towards the proximal end of the catheter along a substantial length of the catheter. The catheter with the balloon are in a multilumen configuration or in a coaxial configuration. A guidewire passage extends through the elastomeric material with the embedded spring. An alternative embodiment illustrates a hub with a movable internal seal and inner tube connected to a balloon catheter tip with a free space collapsement spring. The movable inner seal also assists in spring collapsement and in shortening of the balloon structure for maximum allowable radial inflation. A distal portion of a balloon catheter includes a compressible spring which is free floating within a tubular interior area and having no embedding material about it. A hub is also included for use with a catheter having an extended length balloon. A telescoping tube assembly contains a flared member for front loading of a guide wire.

17 Claims, 15 Drawing Sheets

BALLOON CATHETER

CROSS REFERENCES TO CO-PENDING APPLICATIONS

This patent application is a continuation-in-part of U.S. Ser No. 07/953,481, filed Sep. 29, 1992, now U.S. Pat. No. 5,338,299 entitled "Balloon Catheter", which is a continuation-in-part of U.S. Ser. No. 07/871,722, filed Apr. 21, 1992, now U.S. Pat. No. 5,171,297 entitled "Balloon Catheter," which is a continuation of U.S. Ser. No. 07/324,913, filed Mar. 17, 1989, now U.S. Pat. No. 5,112,304, both assigned to the same assignee as the present patent application.

BACKGROUND OF THE INVENTION

1. Field of the Invention

The present invention pertains to a surgical catheter, and more particularly, a balloon catheter for enlargement of restrictions in blood vessels, arteries or other human tissue.

2. Description of the Prior Art

Prior art balloon catheters have utilized numerous types of structures to expand outwardly to enlarge a restriction such as in a blood vessel, an artery or human tissue, such as the prostrate. One problem in the past with these structures which enlarged on inflation was that the structure did not always return to its original diameter or initial circular configuration.

U.S. Pat. 4,56,000 to Sehjeldahl uses a thin rigid material affixed to the distal end of a catheter to form the balloon. Particularly in the use of nondistensible balloons, the initial profiles achieved by wrapping the balloon are much larger than the outer diameter of the catheter shaft and after inflation in the body, the resulting collapsed profile may appear in cross section as a plate extending outward from the center of the catheter. This necessitates use of a larger device to introduce the balloon catheter and presents complication on removal of the device from the body and may potentially damage tissue.

U.S. Pat. No. 4,637,396 to Cook uses a knitted balloon in which the knitting changes shape to accommodate balloon expansion. This allows for higher pressures to be achieved in larger diameter balloons, but does not necessarily deal with initial or collapsed profiles.

U.S. Pat. No. 4,702,252 to Brooks uses a braided balloon which changes in length as it expands and is accomplished by a spring at the proximal hub end of the catheter. This design requires relative motion between various members of the catheter which may be difficult in long length and tortuous passageways.

U.S. Pat. 4,762,130 to Fogarty uses an embedded spring to lower the profiles of the balloon. This design also requires relative motion along its length and does not enhance the pressure changing capability of the elastomeric materials.

Hubs incorporated in balloon catheters have on occasion exhibited balloon pressure integrity breakdown where pressure is bled off through various sealment members of the hub. One alternative embodiment discloses an additional sealing member within an inner chamber of the hub to provide ample pressure maintaining capabilities for proper and constant pressure balloon inflation.

The present invention overcomes the disadvantages of the prior art by providing a balloon catheter with braided fibers encapsulated between elastomeric materials and an embedded spring to provide a low balloon profile after pressurization and depressurization.

The present invention also overcomes other disadvantages of the prior art by providing a collapsible spring fixed between the movable points for allowing a greater inflational radius.

The present invention also overcomes the disadvantages of the prior art by providing a hub having inner compressible members which aid in the deflation of an extended length balloon. One member of a tubular telescoping assembly provides for internal guidance of a front loaded guide wire.

SUMMARY OF THE INVENTION

The general purpose of the present invention is to provide a balloon catheter which has a low profile in a deflated state after pressurization to a maximum diameter, and to have components which move relative to one another.

According to one embodiment of the present invention, there is provided a balloon catheter with a hub at a proximal end including a guidewire entry port, an inflation/deflation port and a tube connected to the hub. A guidewire passage and an inflation/deflation passage extend along the length of the tube. An embedded spring in an elastomeric material or like material connects to the distal end of the tube. A balloon, including braided fibers encapsulated between an outer elastomeric material and inner elastomeric material, connects between the end of the tube and the distal end of the embedded spring member. The catheter can assume either a multilumen configuration or a coaxial configuration.

According to an alternative embodiment of the present invention, there is provided a hub for use with a balloon catheter having an additional seal incorporating an O-ring aligned about a piston in direct contact with an internal chamber of the hub, thus providing a seal to contain pressurized fluid.

According to another alternative embodiment of the present invention, there is provided a balloon catheter distal end incorporating a free space spring having unrestricted movement for the purpose of returning a balloon to its streamlined relaxed position after it has been inflated. The tip member is connected by a movable tube connected to a piston member, which assists in negation of the spring function during inflation, as well as shortening of the distal tip/balloon area length to allow for greater radiused inflation.

According to yet another embodiment of the present invention, there is provided a hub member for use where a balloon is incorporated in a catheter. Internal members compress to assist in balloon inflation, and decompress to a memory position to aid in balloon deflation by positioning an inner tube member, which attaches to the distal end of the inflatable balloon. A telescoping assembly having an outer tube member and a flared inner tube member assist in guidance of a distally loaded guide wire.

Significant aspects and features of the present invention include a low profile balloon before and after pressurization to its maximum diameter. The differential between the balloon structure and the inner member of the catheter is minimal, even after pressurization and subsequent depressurization because of the combined action of the internal spring and the elastomeric material of the balloon. The pliability of the elastomeric material and the spring also provide enhanced steering of the catheter during placement due to its extreme flexibility and soft tip.

Other significant aspects and features of the present invention is the ability to achieve higher balloon pressures, especially in larger sized balloons used in larger vessels, arteries or tissues.

Additional significant aspects and features of the present invention include a braided fiber member which expands to a fixed diameter on inflation with enhanced pressure conveying capability. The braided fibers assist the balloon to collapse to approximately the same profile after pressurization. Additionally, there is enhanced cyclic durability because of the elastomeric materials.

In addition, the use of fibers and elastomeric materials in the balloon construction provides for a softer distal tip to the catheter, enhancing steerability and reducing trauma. In addition, the elastomeric material provides a construction which enhances its ability to withstand repeated cycles of pressurization and depressurization.

In addition, the braid can be made of a radiopaque material obviating the need for specific bands for locating the balloon in the body under fluoroscopy. The embedded spring also provides structural integrity against collapse of the inner member of the catheter during pressurization of the balloon. This enhanced ability allows for movement of the guidewire while the balloon is pressurized.

A further significant aspect and feature of the present invention includes a connecting tube between the sealing member piston and tip to distend the balloon catheter in a proximal direction where the effect of spring tension along the balloon structure is relaxed and negated.

Yet still another significant aspect and feature of the present invention is a balloon structure whose length is essentially shortened, thus allowing a greater radius of inflation.

Still another significant aspect and feature of the present invention is a hub having an internal piston, which is pressurized, and simultaneous energy is stored while allowing proximal positioning of a balloon catheter inner tube to correspond with the shortening of a balloon during inflation. Energy is released when depressurizing to cause positioning of a balloon catheter inner tube distally to aid in collapsing the balloon.

The hub where the energy of compression of material or air or both is utilized to distend distally an inner catheter tube to assist in collapsing and deflating of the balloon.

Yet another significant aspect and feature of the present invention is a tubular extension system internally located to offer guidance to a distally loaded guide wire which is positioned proximally.

Having thus described embodiments of the present invention, it is a principal object hereof to provide a balloon catheter with a balloon using braided fibers or like materials disposed between an inner and an outer Elastomeric layer.

One object of the present invention is to provide a multilumen balloon configuration or a coaxial balloon configuration.

Another object of the present invention is to provide a balloon catheter which includes internal structure which functions to deflate and collapse the balloon after pressurization to its maximum diameter. The balloon with braided fibers between the elastomeric material returns to its normal position, and a spring embedded in an elastomeric material of the distal end of the catheter further functions to collapse and return the balloon to a normal, deflated position after pressurization. A material with a like function can also be utilized in place of the spring.

Still another object of the present invention is to provide a spring structure bonded at its ends and at movable points and in a tubular area which functions to deflate and collapse the balloon after pressurization to its maximum diameter. The balloon structure with braided fibers between the elastomeric material returns to its normal position aided by the spring which is unrestricted in movement.

Yet another object of the present invention is to provide a hub having predetermined piston travel to help determine the maximum radius of balloon structure inflation.

Additionally, another object of the present invention is to provide a well sealed leak proof hub for maintaining proper inflational pressures. A further object of the present invention is to provide a hub for use in inflation and deflation of the balloon.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
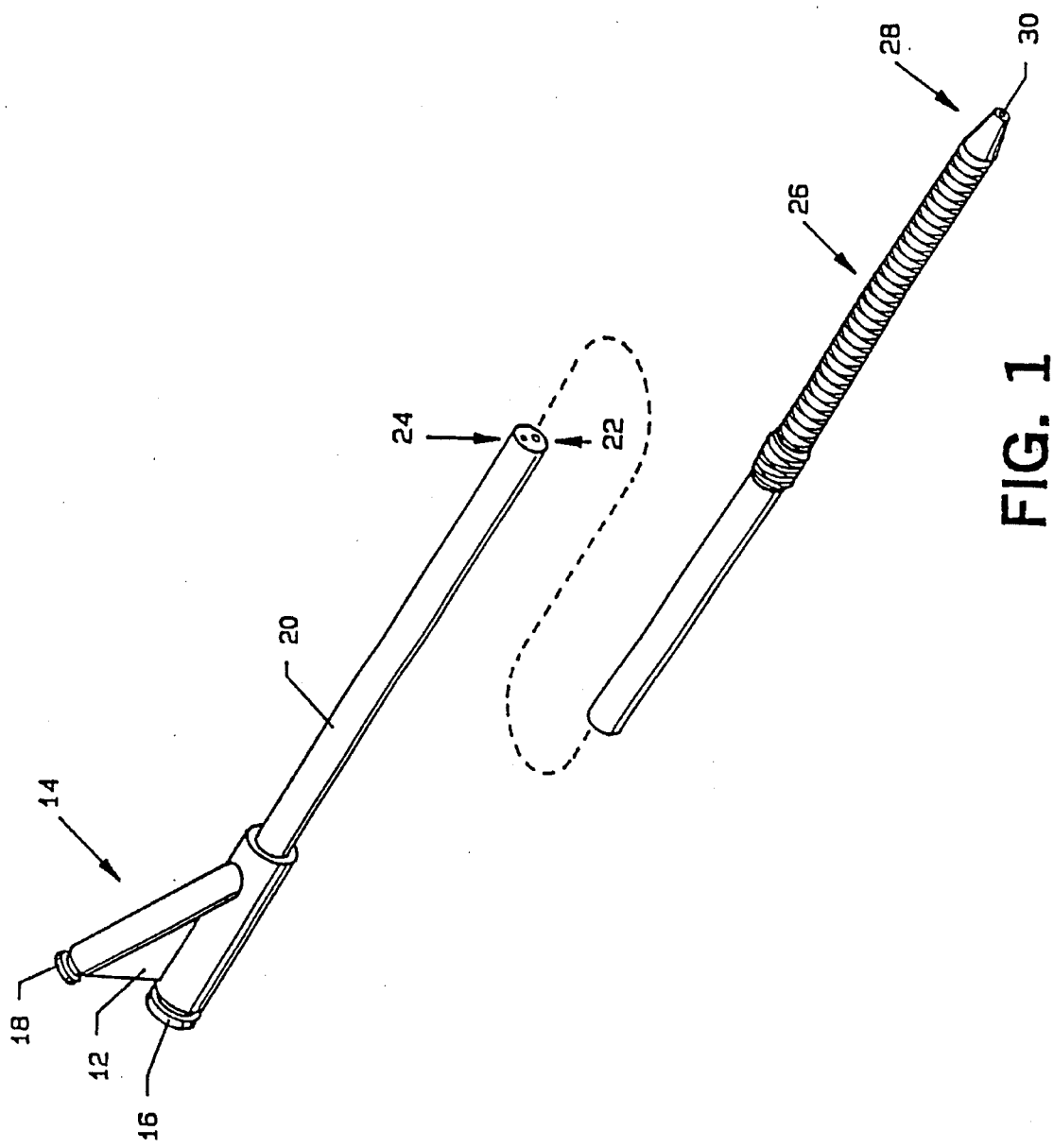
FIG. 1 illustrates a perspective view of a multilumen balloon catheter, the present invention.

FIG. 1 illustrates a perspective view of a multilumen balloon catheter 10, the present invention, including a hub at a proximal end 14 with guidewire entry port 16 and an inflation/deflation port 18. This particular multilumen configuration is bilumen. A catheter tube 20 connects to the hub 12, and includes a guidewire passage 22 and an inflation/deflation passage 24. A balloon structure 26, as later described in detail, secures about the distal end 28. A guidewire exit 30 is at the distal end 28 of the balloon structure 26.

Figure 2:
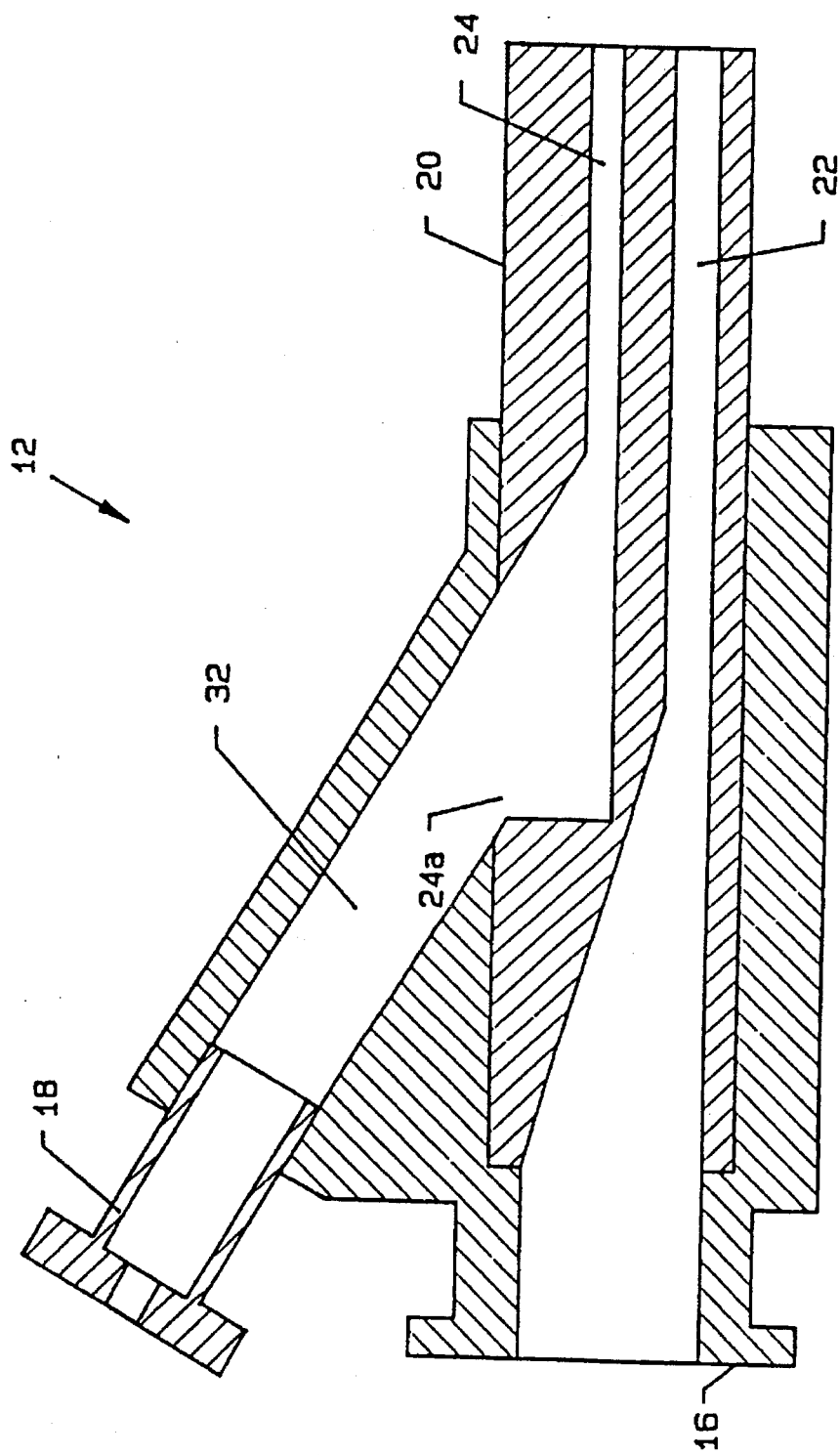
FIG. 2 illustrates a cross-sectional view of the hub of the multilumen configuration.

FIG. 2 illustrates a cross-sectional view of the hub 12 where all numerals correspond to those elements previously described. The figure illustrates the hub 12 being a molded thermoplastic member engaged about the catheter tube 20, and fused or adhesively secured thereto. The hub 12 includes a hub chamber 32, an inflation/deflation port 18, and a guidewire entry port 16. The proximal end of the catheter tube 20 secures into one end of the guidewire entry port 16. The hub 12, the catheter tube 20, the guidewire entry port 16 and the inflation/deflation port 18 are assembled by known processes. The guidewire passage 22, internal to the catheter tube 20, connects between the guidewire entry port 16 and the balloon structure 26 of FIG. 3. The inflation/deflation passage 24 connects the balloon structure 26 to the inflation/deflation port 18 through an angled passageway 24a and the hub chamber 32.

Figure 3:
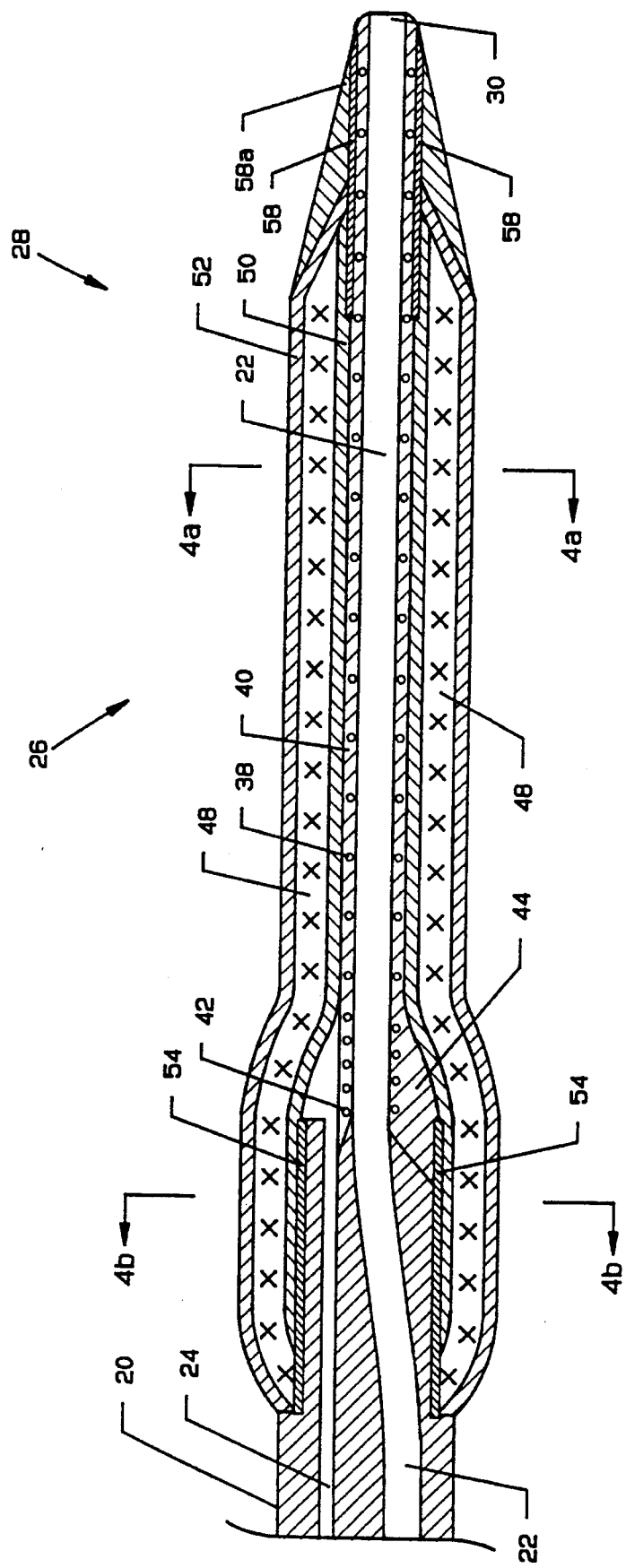
FIG. 3 illustrates a cross-sectional view of the distal end of the multilumen configuration.

FIG. 3 illustrates a cross-sectional view of the distal end 28 of the balloon catheter 10. An embedded spring 38 is embedded or fused into elastomeric material 40 which connects to the catheter tube 20 at point 44, such as by heat fusion or adhesively. The spring can be tensioned to a predetermined degree prior to being embedded in the elastomeric material providing a memory for the embedded spring 38 in the elastomeric material. A balloon structure 26, which is coaxial, includes a braided fiber 48 between an inner elastomeric material 50 and outer elastomeric material 52, which is secured about point 54 of the catheter tube 20 and about point 58 of the embedded spring 38 and elastomeric material 40 containing the guidewire passage 22, such as by heat fusion or adhesively. The molded tip 58a provides flexibility and softness of the catheter.

Figure 4B:
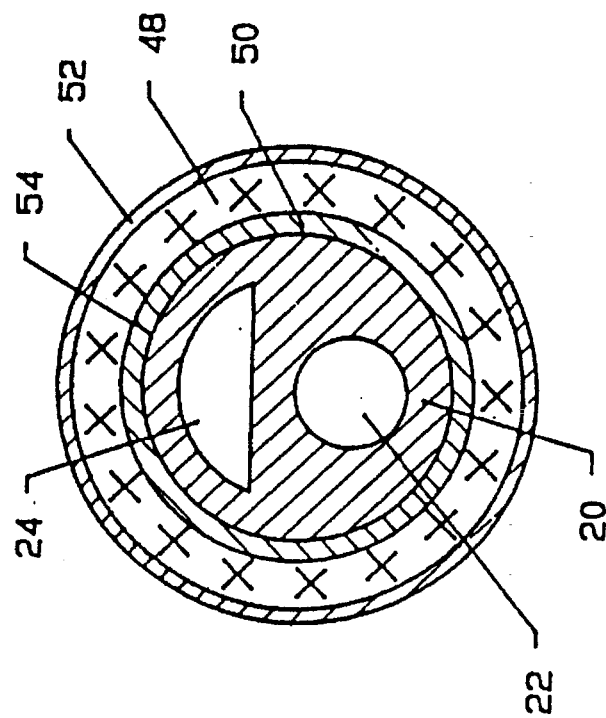
FIG. 4B illustrates a cross-sectional view taken along line 4b–4b of FIG. 3 of the multilumen configuration.
Figure 4A:
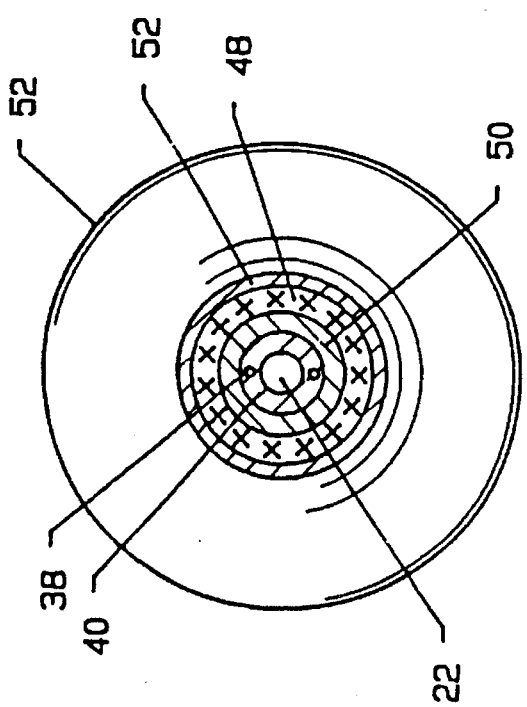
FIG. 4A illustrates a cross-sectional view taken along line 4a–4a of FIG. 3 of the multilumen configuration.

FIG. 4A illustrates a cross-sectional view taken along line 4a–4a of FIG. 3 where all numerals correspond to those elements previously described.

FIG. 4B illustrates a cross-sectional view taken along line 4b–4b of FIG. 3 where all numerals correspond to those elements previously described.

Figure 5:
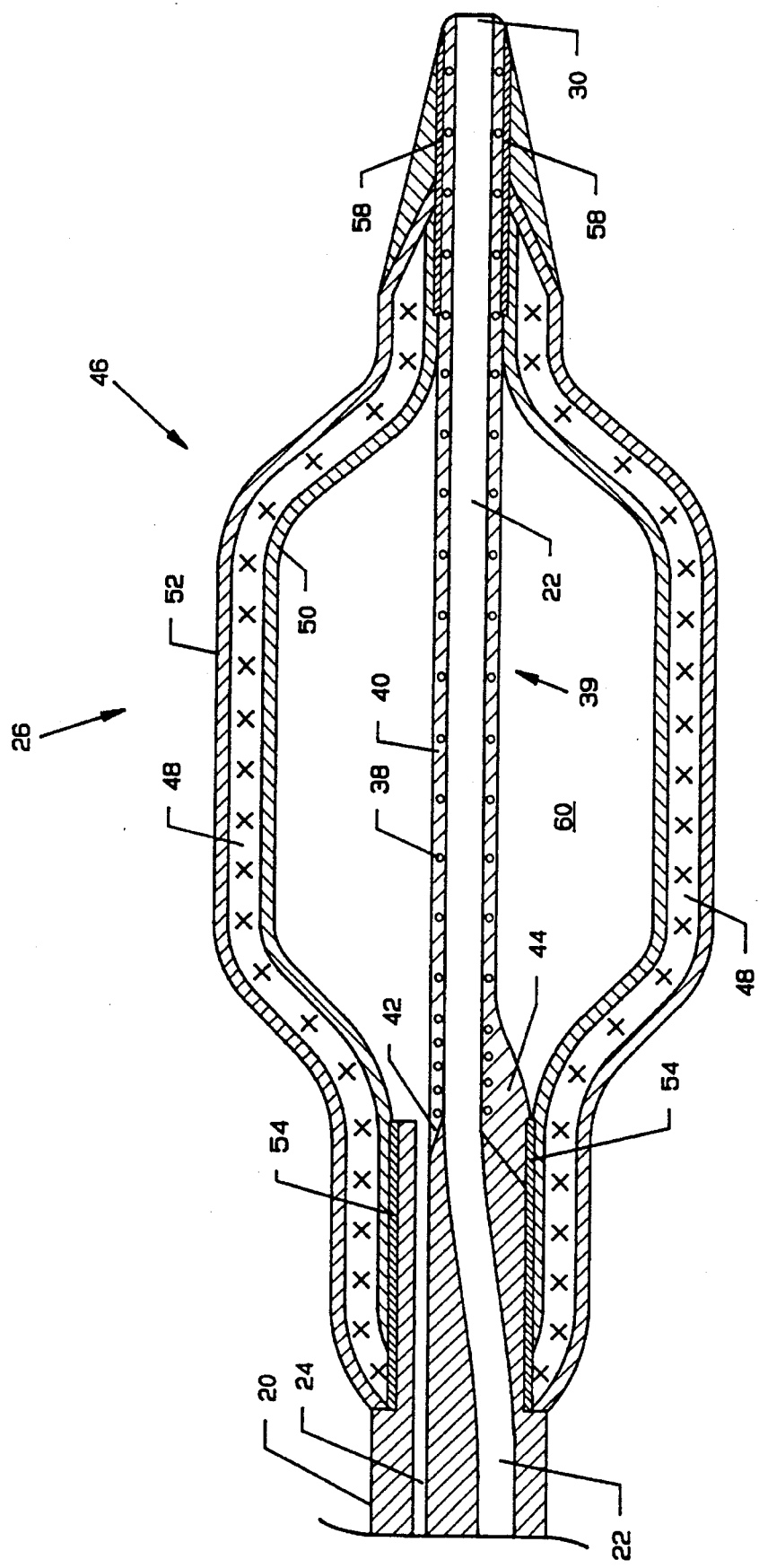
FIG. 5 illustrates the expanded balloon of the multilumen configuration.

FIG. 5 illustrates the balloon catheter 10, particularly, the balloon structure 26 in an inflated balloon position 46. All numerals correspond to the elements previously described. The embedded spring is compressed longitudinally and the braided fiber has been expanded outwardly so as to enlarge along substantial portion of its length centered approximately the mid-point of the longitudinal length of the braided fibers. The outward expansion of braided fibers 48 effectively shortens the length the balloon 26 in a direction towards the proximal causing the embedded spring 38 to compress in a like direction. The braided fibers 48 provide for expansion to a predetermined diameter for the balloon, and form cavity 60 about the inner surfaces of the balloon structure 26 and the member with the embedded spring 38. After deflation of the inflated balloon position 46 and placing a vacuum on the inflated balloon and position 46 through the inflation/deflation port 18, the elastomeric materials 50 and 52 about the braided fibers 48 in combination, provide for collapsing of the balloon, as well as the embedded spring 38 returning to a normal resting position. Likewise, the memory of the elastomeric material materials 50 and 52 and the embedded spring 38 secondarily assist the balloon structure in returning to a predetermined collapsed condition. Materials of known elasticity can be selected such that the braided fibers or the spring may not be required. The elastomeric materials can also be selected to have different degrees of elasticity for expansion and subsequent contraction.

MODE OF OPERATION

Referring to FIGS. 1–5, during a typical procedure, a guidewire is placed through a body tube or tissue to be dilated, typically an artery. The balloon catheter 10 is then introduced over the guidewire by placing the distal end 28 of the catheter over the proximal end of a guidewire. The balloon catheter 10 is then moved into a position of restriction by moving the catheter over the guidewire. Once in position, a syringe filled with a radiopaque fluid is attached to the inflation/deflation port 18 and the syringe plunger moved inward to inflate and pressurize the inflated balloon position 46 by passing radiopaque fluid through the inflation/deflation passage 24 and into the cavity 60 to—expand the balloon structure 26 outwardly to a desired intermediate expansion point or to a maximum expansion point allowed by the weave structure of the braided fibers 48. After inflation, a vacuum is introduced into the balloon by moving the plunger outward. The balloon then returns to its resting position. The catheter is then removed from the body. The balloon is caused to return to its normal deflated position by the braided fibers seeking to return to a resting position, the elasticity of the materials and the embedded spring 38.

DESCRIPTION OF A FIRST ALTERNATIVE EMBODIMENT

Figure 6:
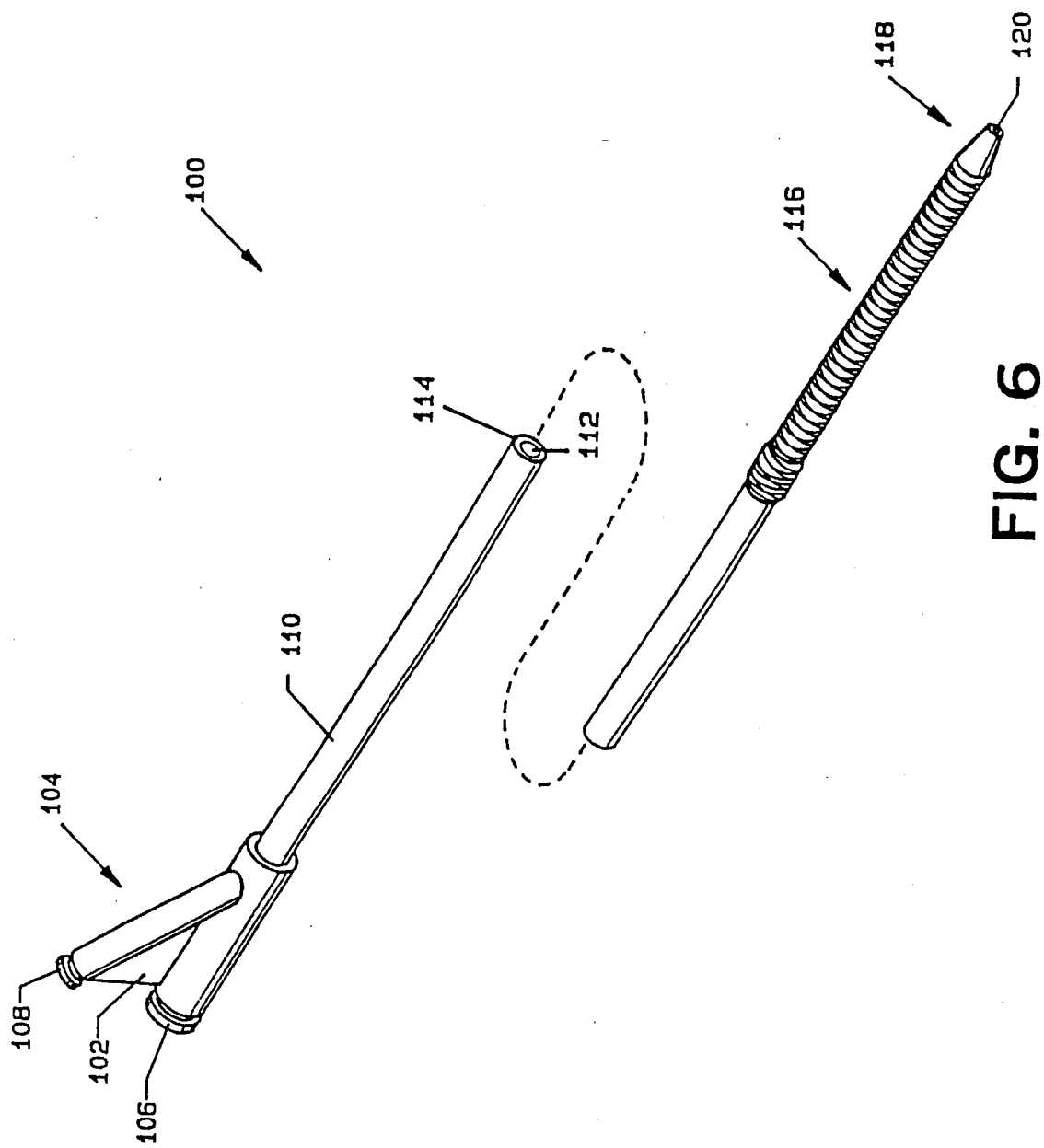
FIG. 6 illustrates a perspective view of a coaxial balloon catheter, an alternative embodiment of the present invention of the coaxial configuration.

FIG. 6 illustrates a perspective view of a coaxial balloon catheter 100, an alternative embodiment of the present invention, including a hub 102 at a proximal end 104 with guidewire entry port 106 and an inflation/deflation port 108. A coaxial catheter tube 110 connects to the hub 102, and includes a guidewire passage 112 and an inflation/deflation passage 114. A balloon structure 116, as later described in detail, secures about the distal end 118. A guidewire exit 120 is at the distal end 118 of the tube 110. The principles of the alternative embodiment are like those as described in FIGS. 1–5.

Figure 7:
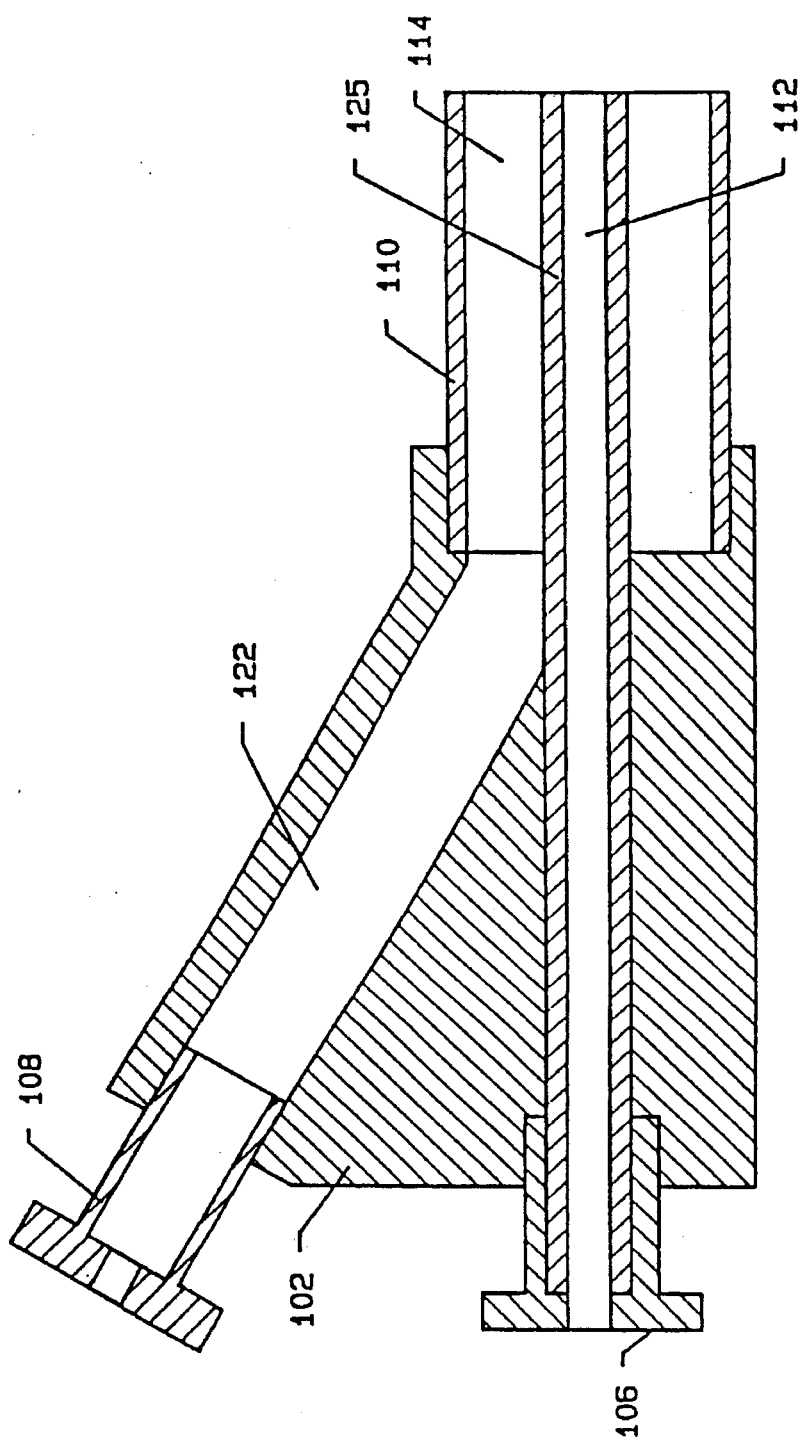
FIG. 7 illustrates a cross-sectional view of the hub of the coaxial configuration.

FIG. 7 illustrates a cross-sectional view of the hub 102 where all numerals correspond to those elements previously described. The figure illustrates the hub 102 being a molded member engaged about the tube 110 and fused or adhesively secured thereto. The hub 102 includes a hub chamber 122, an inflation/deflation port 108, and a guidewire entry port 106 secured into the hub 102. The proximal end of the tube' 110 secures into one end of the guidewire entry port 106. The hub 102, the tube 110, the guidewire entry port 106 and the inflation/deflation entry port 108 are assembled by known processes. An inner coaxially aligned tube 125 forms the guidewire passage 112 and connects between the guidewire entry port 106 and the balloon structure 116 of FIG. 8. The inflation/deflation passage 114 is formed between the walls of the tube 110 and the elastomeric material 125 in a coaxial fashion. The inflation/deflation passage 114 connects the balloon structure 116 to the inflation/deflation port 108 through the hub chamber 122 as illustrated in FIG. 8.

Figure 8:
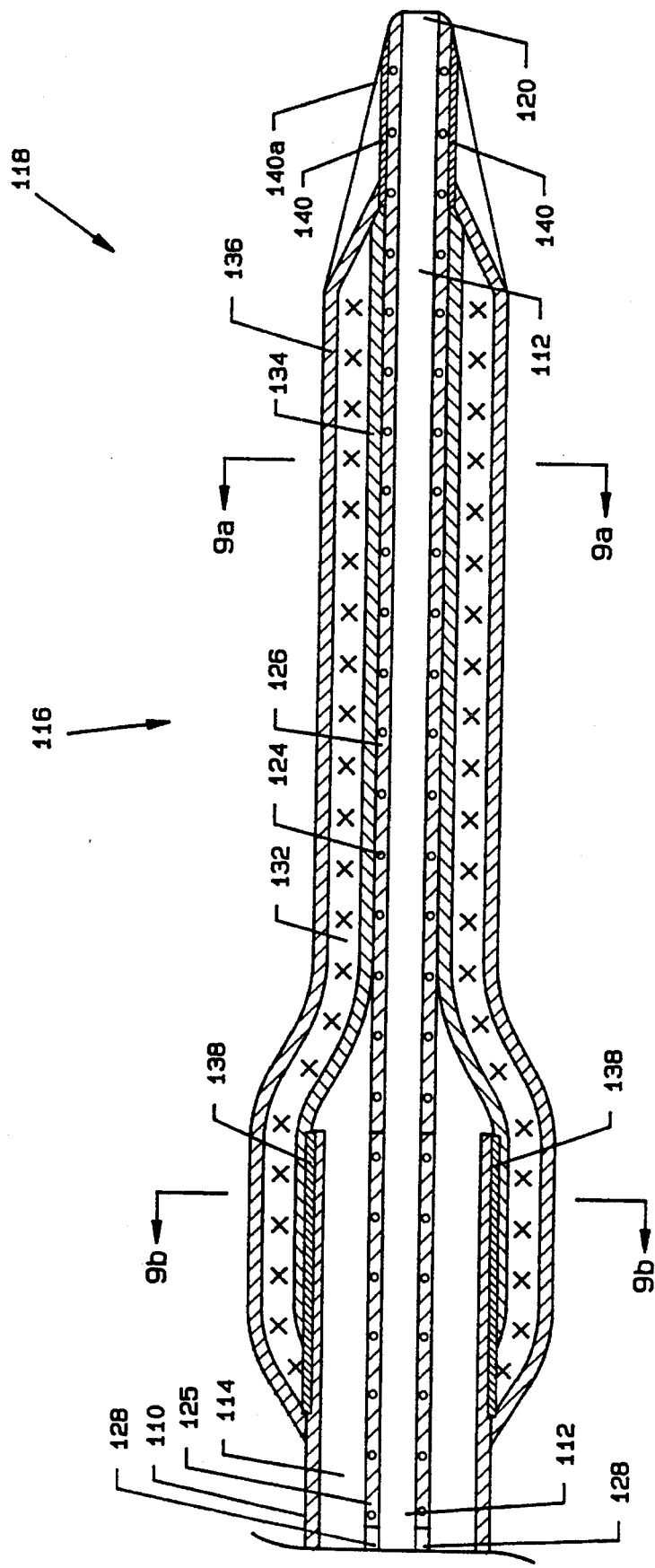
FIG. 8 illustrates a cross-sectional view of the distal end of the coaxial configuration.

FIG. 8 illustrates a cross-sectional view of the distal end 118 of the balloon catheter 100. An embedded spring 124 is embedded in elastomeric material 126 which connects to the tube 110 at point 128, such as by heat fusion or adhesive. The embedded spring 124 can be tensioned to a predetermined degree prior to being embedded in the elastomeric material providing a memory for the embedded spring in the elastomeric material. A balloon structure 116 which is coaxial includes an inner braided fiber 132 between an inner elastomeric material 134 and an outer elastomeric material 136, secures about point 138 of the tube 110 and about point 140 of the embedded spring 124 and inner elastomeric material 126 containing the guidewire passage 112 such as by heat fusion or adhesively. The molded tip 140a provides flexibility and softness of the catheter.

Figure 9A:
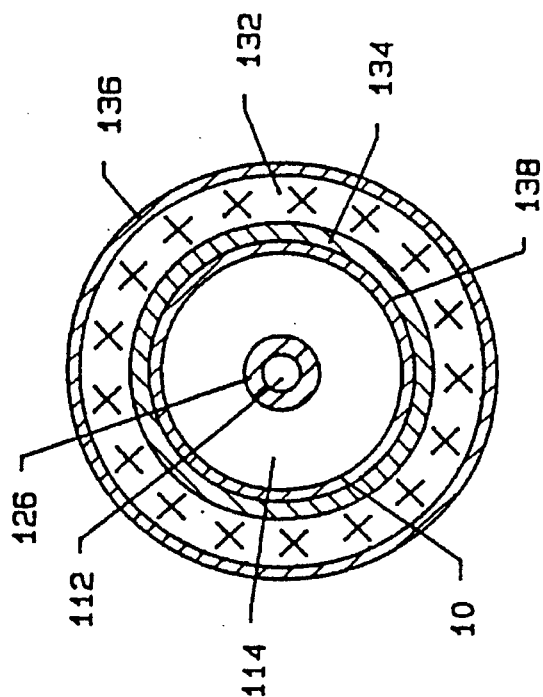
FIG. 9A illustrates a cross-sectional view taken along line 9a–9a of FIG. 8 of the coaxial configuration.

FIG. 9A illustrates a cross-sectional view taken along line 9a–9a of FIG. 8 where all numerals correspond to those elements previously described.

Figure 9B:
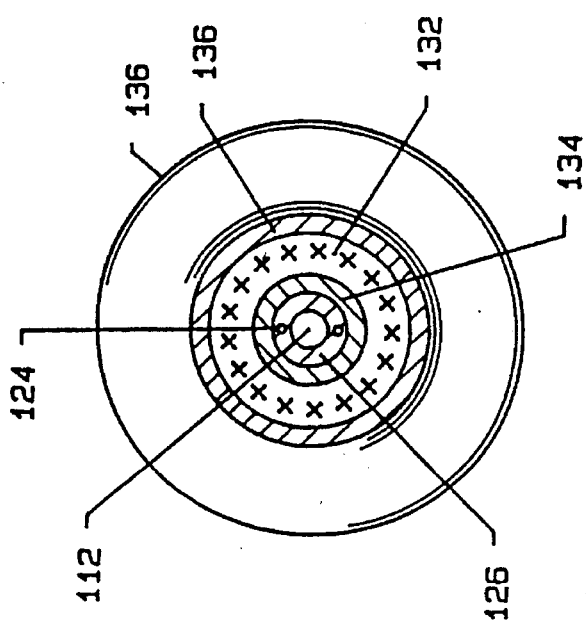
FIG. 9B illustrates across-sectional view taken along line 9b–9b of FIG. 8 of the coaxial configuration.

FIG. 9B illustrates a cross-sectional view taken along line 9b–9b of FIG. 8 where all numerals correspond to those elements previously described.

Figure 10:
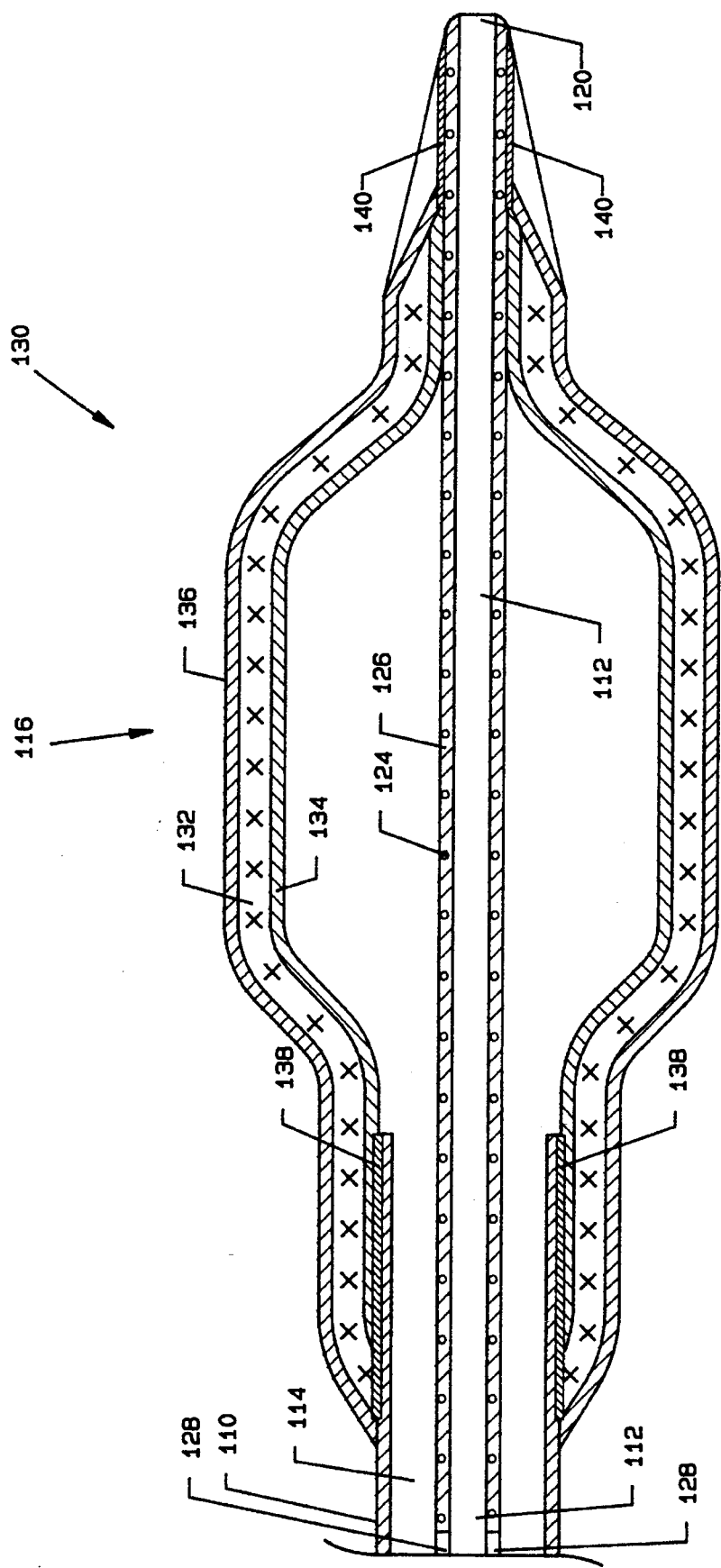
FIG. 10 illustrates the expanded balloon of the coaxial configuration.

FIG. 10 illustrates a balloon catheter 100, and particularly the balloon 130 in an inflated mode position. All numerals correspond to those elements previously described. The operation is similar to that as described for FIGS. 1–5.

DETAILED DESCRIPTION OF A SECOND ALTERNATIVE EMBODIMENT

Figure 11:
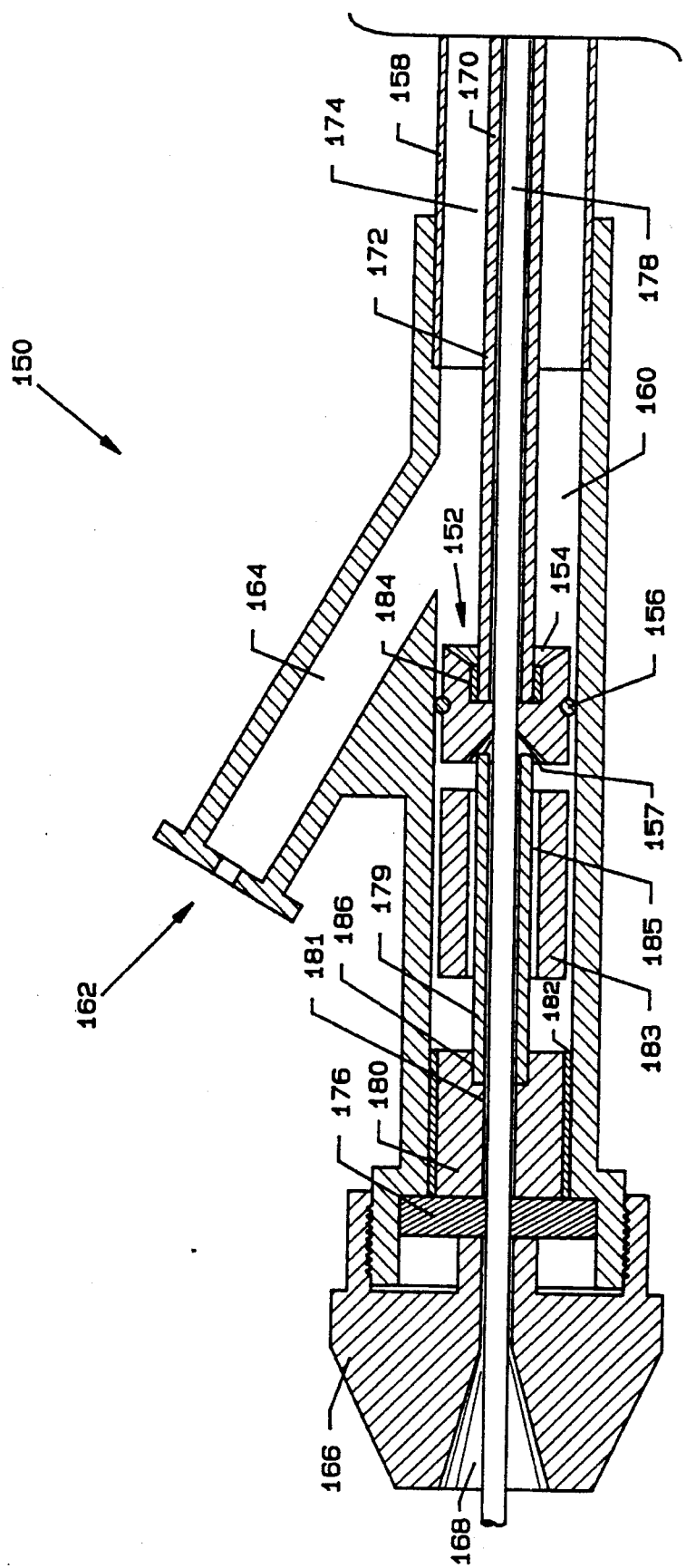
FIG. 11 illustrates a cross-sectional view of a hub including an additional sealing member of a second alternative embodiment.
Figure 12:
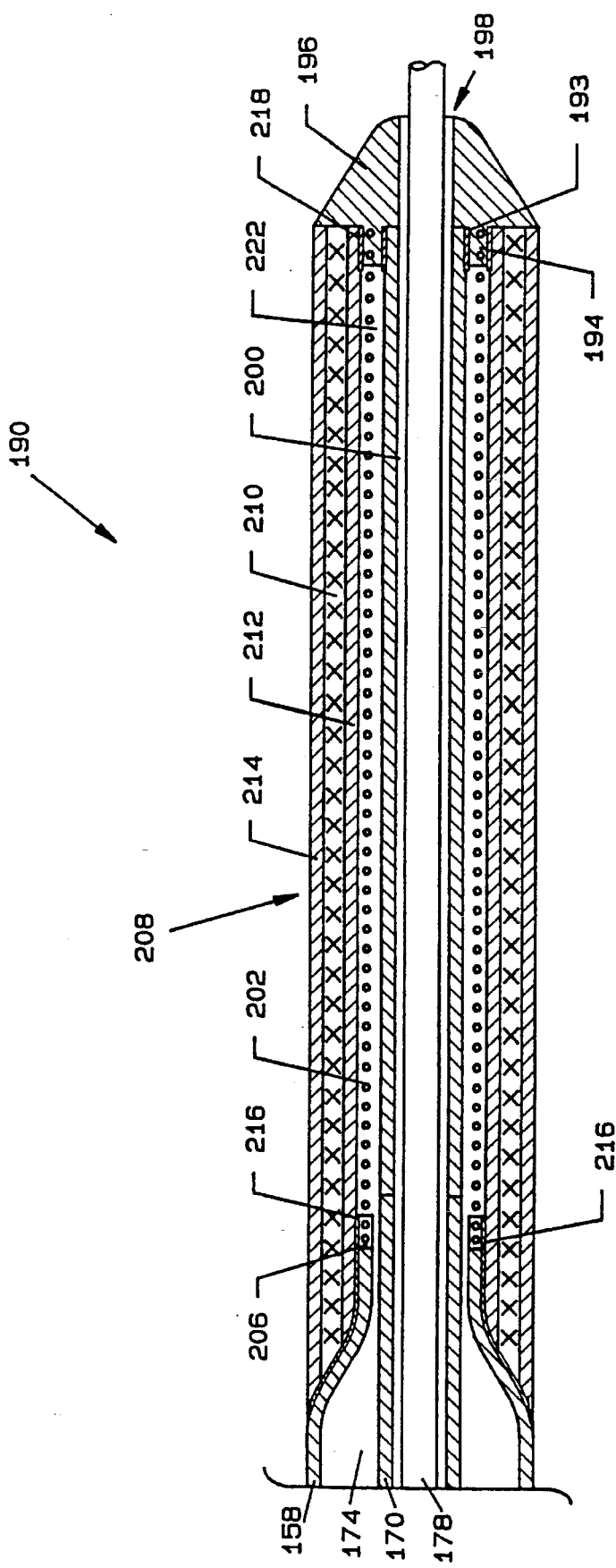
FIG. 12 illustrates a cross-sectional view of a distal end of a balloon catheter of a first alternative embodiment.

FIG. 11, a second alternative embodiment, illustrates a cross-sectional view of a hub 150 for use with a balloon catheter 190 such as illustrated in FIG. 12 which utilizes a sealing member 152 comprised of a piston 154, an O-ring or quad ring 156, a tapered conical surface 151, and other members as now described. The figure illustrates the hub 150 being a molded member engaged about a tube 158 and fused or adhesively secured thereto. The hub 150 includes a hub chamber 160, an inflation/deflation port 162, an inflation/deflation chamber 164 between the inflation/deflation port 162 and the hub chamber 160, a cap 166 threadingly secured over the proximal end of the hub 150, and a guidewire entry port 168 centered through the axis of the cap 166. The proximal end of the tube 158 secures into one end of the hub 150. The hub 150, the tube 158, the guidewire entry port 168 and the inflation/deflation port 162 and associated members are assembled by known processes. An inner coaxially aligned elastomeric tube 170 aligns within the tube 158 and serves as a guidewire passage 172 and connects between a balloon structure such as balloon structure 116 of FIG. 8 or the balloon structure 208 of FIG. 12 and passes through the hub chamber 160 and secures to the piston 154 of the sealing member 152 as later described in detail. An inflation/deflation passage 174 is formed between the walls of the outer tube 158 and the tubular elastomeric material 170 in a coaxial fashion. The cap 166 is threaded onto the end of the hub 150 and compresses a seal 176 through which a guidewire 178 passes. A cylindrical stop cylinder 180, including a central bore 181, aligns at the proximal end of the hub chamber 160 and secures thereto by a bonding glue 182 or other suitable means. A stainless steel hypo tube 179 is form fit, press fit, bonded or otherwise secured to an annular recess 186 in the cylindrical stop cylinder 180 and extends to align with the tapered conical surface 156 of the sealing member 152. The hypo tube 179 provides for passage of the guidewire 178 through the various members, including a compressible rubber cylindrical buffer 188, a sealing member 152 and the elastomeric tube 170. A compressible rubber cylindrical buffer 183, such as silicone rubber, or soft plastic, and having a bore 185 slightly larger than the hypo tube 179 acts as a shock absorber and slidingly aligns over and about the stainless steel hypo tube 179. The piston 154 of the sealing member 152 slidingly engages the guidewire 178 and is secured to the proximal end of the elastomeric tube 170 by a bonding glue 184 or other suitable means. The overall length of piston 154, along with the length of the compressible rubber buffer 183, control the length of travel of the piston 154 and the elastomeric tubing 170. The O-ring seal 156 about the piston 154 seals against the inner wall of the hub chamber 160 to provide a pressure seal between proximal and distal portions of the hub chamber 160. Pressurizing fluid injected into the inflation/deflation port 162 is sealed from the dry proximal end of the hub chamber 160 containing only air by the piston 154 and the O-ring seal 156 about the piston 154. As pressurization of the balloon takes place, the spring member of the balloon is compressed and the overall balloon length is shortened as the elastomeric tube 170 is slidingly projected in the proximal direction by piston action of the sealing member. The piston 154, the O-ring seal 156 and the elastomeric tube 170, accordingly slide proximally along the guidewire 178 in the hub chamber 160 until the point of maximum restricted balloon inflation or until the piston 154 causes the cylindrical rubber buffer 183 to compressingly engage the cylindrical stop cylinder 180. The sealing member 152 maintains inflational integrity of an attached balloon catheter allowing the balloon structure 208 pressure to remain proper and constant where prior art devices have not maintained proper and constant pressure due to leakage in areas such as the cap seal.

FIG. 12 illustrates a cross-sectional view of a distal end of a balloon catheter 190 having a spring in a free space tubular area which is unrestricted by embedding materials, such as for use with a hub 150, such as illustrated in FIG. 11. All other numerals correspond to those elements previously described. A tubular elastomeric member 170 is located along the longitudinal axis and aligns in and is bonded by a bonding glue 193 to the interior of a tubular member 194 extending from a soft and flexible molded tip 196. A guidewire passage 198 in the molded tip 196 aligns with the guidewire passage 200 central to the elastomeric tube 170 along the longitudinal axis. One end of a spring 202 is embedded in the tubular member 194 of the tip 196 and extends coaxially over and about and along the interior of the elastomeric tube 170 until it meets and connects to tube member 158. Tube member 158 flares downwardly to meet the proximal end of the spring 202 and is secured thereto by a plastic shrink tube connector 206 or by other suitable means. The spring 202 can also butt up against tube 158 without being bonded. A coaxial balloon structure 208 aligns coaxially over and about the elastomeric tube 170, the spring 202 and the flared end of the tube 158. The balloon structure 208 includes an inner braided fiber 210 between an inner elastomeric material 212 and an outer elastomeric material 214 secured about the necked down portion of the tube 158 and about the tubular extension member 194 of the tip 196, such as by heat fusion or adhesive bonding 216 and 218. Pressurized inflation fluid from the inflation/deflation passage 174 transmits pressure along the area 222 between the elastomeric tube 170 and the inner elastomeric material 212 in which the spring 202 resides to inflate the balloon structure 208 as illustrated in FIG. 13.

Figure 13:
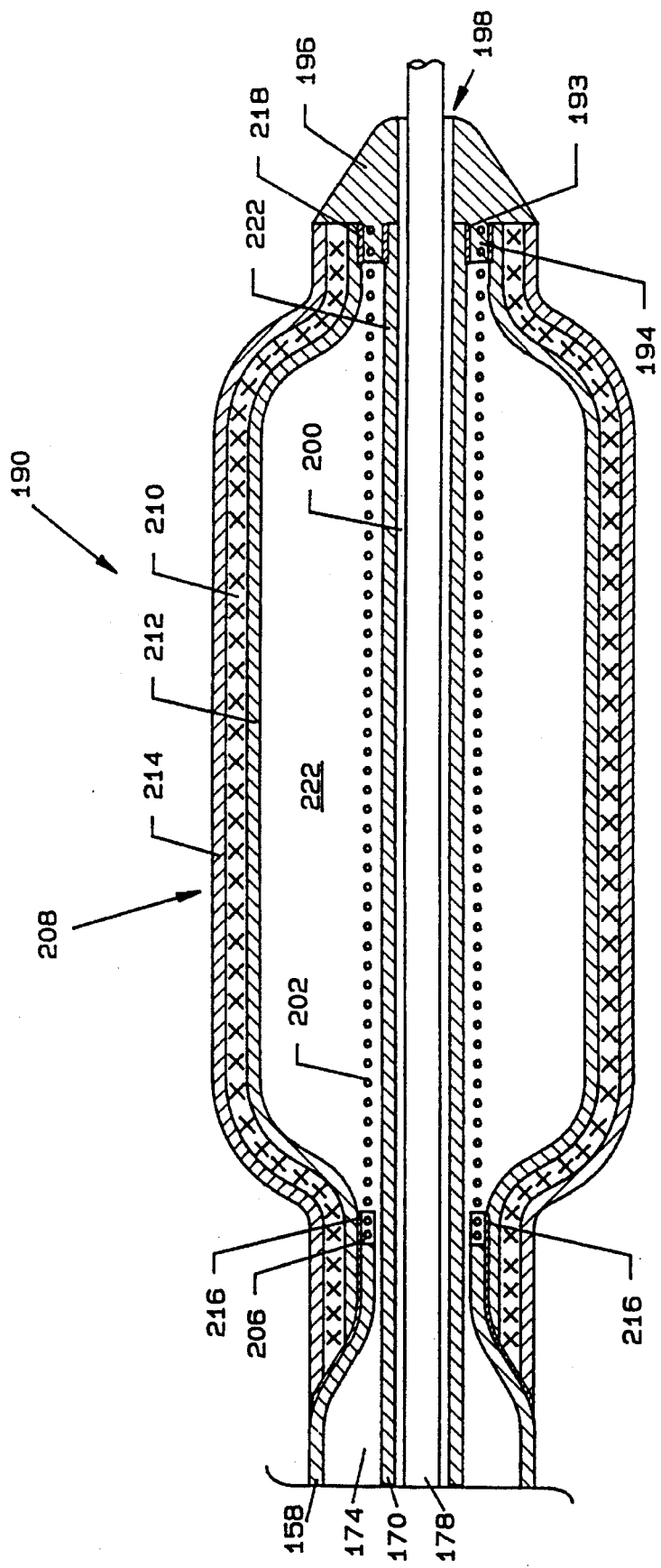
FIG. 13 illustrates the balloon structure of FIG. 12 in the inflated position.

FIG. 13 illustrates the balloon structure in the inflated mode of operation where all numerals correspond to those elements previously described. The overall length of the distal end of the balloon catheter 190 is shortened during the inflation process due to the qualities of the elastomeric materials incorporated. The spring 202 is compressed along the longitudinal axis during inflation and expands along the longitudinal axis during deflation to aid and assist in returning the balloon structure 208 to the streamlined position as illustrated in FIG. 12.

MODE OF OPERATION OF THE SECOND ALTERNATIVE EMBODIMENT

The mode of operation of the second alternative embodiment is best described with reference to FIGS. 11, 12 and 13. First the maximum amount of expansion of the balloon catheter balloon structure 208 is determined. A hub 150 having a piston 154 and a rubber buffer cylinder 183 of suitable length is then chosen to accommodate the maximum amount of desired balloon structure 208 inflation. The hub 150 and the balloon catheter 190 are then fit over and slid over, about and along the guidewire 178 by known means until reaching the point of desired inflation. The cap 166 is then tightened on the hub threads to cause the seal 176 to compress about and to seal the guidewire 178, thus forming the primary seal of the hub chamber 160 at a point proximal to the sealing member 152. Saline solution is positive pressure fed through the inflation/deflation port 162 and travels through the inflation/deflation port 162 to the hub chamber 160. Positive pressure in the hub chamber is exerted in two directions, distally through the tube 158 to the balloon structure 208 and proximally toward the piston 154 of the sealing member 152. As positive system pressure increases, saline pressurizes the area 222 between the inner circumferential surfaces of the inner elastomeric material 212 causing the balloon structure 208 to expand outwardly to enlarge restricted blood vessels, arteries, or other bodily structures. Pressure exerted against the sealing member 152 drives the sealing member 152 a finite distance proximally until the sealing member 152 compresses the flexible rubber buffer 183 against the cylindrical stop cylinder 180. As the sealing member 152 is driven a finite distance proximally, the inner tube 170 also correspondingly moves proximally with respect to the tube 158 to position the balloon catheter tip 196 in a proximal direction. This action accomplishes several tasks. Firstly, the spring 202 is compressed, thus rendering the action of the spring 202 null and void for this part of the procedure. This is particularly important in that in the deflated mode, the spring tension which causes the balloon structure to become streamlined is overcome. Negating of the spring force cancels the stretching force along the length of the balloon structures 208 and allows the balloon structure 208 to be inflated outwardly without hindrance from an outstretched spring. Secondly, this action' shortens the balloon structure 208, thus allowing a greater radius of expansion for the balloon structure 208 as it is suspended between two points 216 and 218 which are not fixed as in prior art devices, butt which are laterally moveable.

Deflation of the balloon structure 208 is accomplished in a reverse order. Pressure at the inflation/deflation port 162 is reduced to zero or can be reduced to a negative pressure if so required. The sealing structure 152 and the inner tube 170 then return to their relaxed mode position with the release of positive system pressure and with assistance from the compressed spring 202, which then returns to its normal length which also returns the balloon structure 208 to its original streamlined low profile position.

DESCRIPTION OF A THIRD ALTERNATIVE EMBODIMENT

Figure 14:
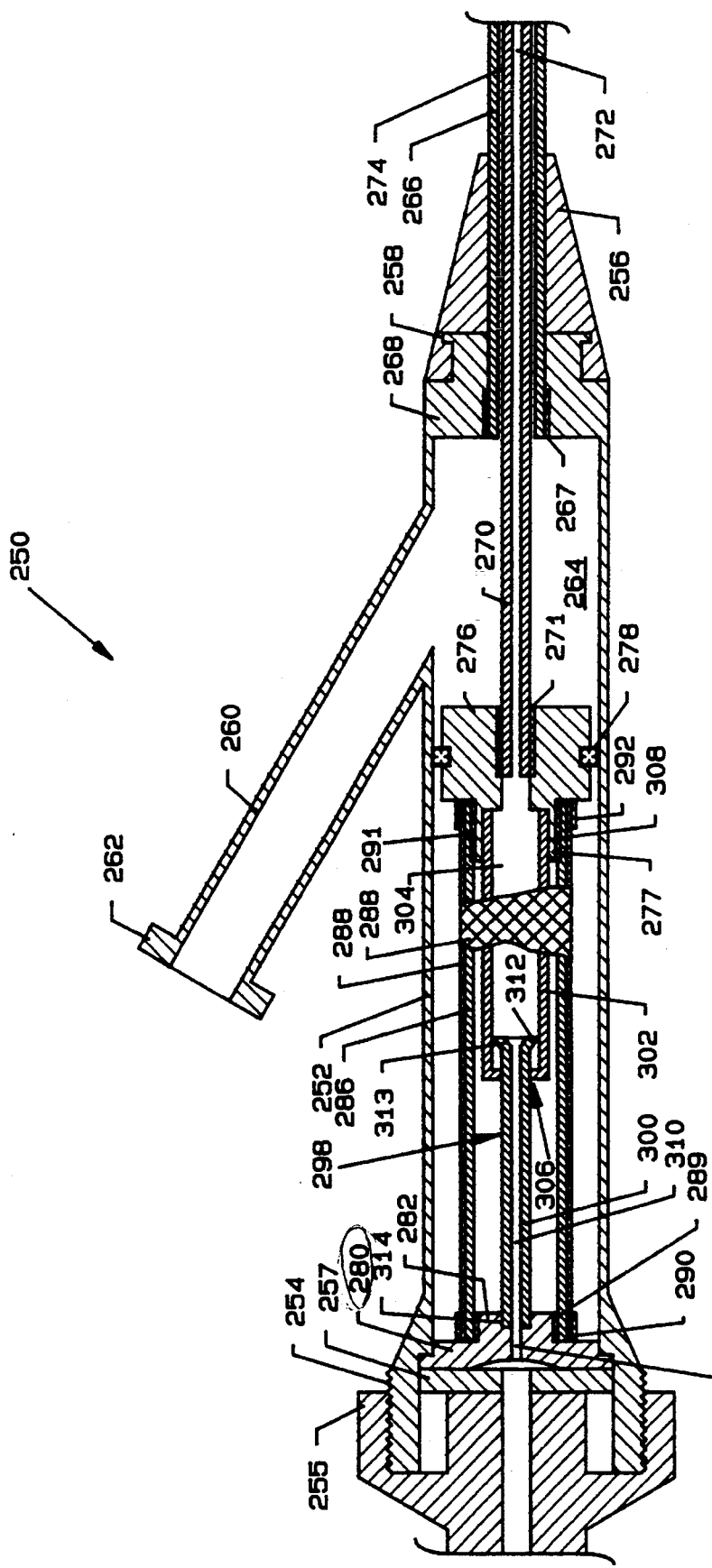
FIG. 14 illustrates a cross-sectional view of a third alternative embodiment of a hub for use with extended length balloons in the depressurized mode; and, FIG. 15 illustrates a cross-sectional view of a hub for use with the balloon in a pressurized mode.

FIG. 14 illustrates a cross-sectional view of a hub 250 for use with a balloon or an extended length balloons of, for purposes of example only, lengths up to 12 cm. Members interior to the hub 250 assist in returning a balloon, such as a balloon of an extended length balloon to a substantially full and uninflated length of substantially original cross section. The hub 250 includes a central tubular member 252 having at one end a threaded portion 254 for connection to a Touhy Borst connector 255, and on the opposite end a flexible rubber like conical tip 256 affixed to the central tubular member 252 over and about an annular rim 258. An inflation port 260, having a connector flange 262, aligns at an angle to the central tubular member 252 and is plumbed to the central bore 264 of the central tubular member 252. A flexible polymer tube 266 aligns and suitably secures by bonding glue 267 through the distal end 268 of the hub 250. A polyimide tube 270, having a guidewire lumen 272, slidingly aligns in the lumen 274 of the polymer tube 266, and is secured by suitable bonding glue 271 to a piston 276. Sufficient clearance between the interior wall of the flexible polymer tube 266 and the outer wall of the polyimide tube 270 allows for inflation of a balloon at the distal end of the balloon catheter. The polyimide tube 270 secures by a bonding glue 271 to the piston 276 aligned in the central bore 264. A connection nipple 277 extends from one side of the piston 276. The piston 276 is sealed against the interior walls of the central bore 264 by a quad ring seal 278, thus creating a sealed pressurized system including a balloon as previously illustrated at the end of the flexible polymer tube 266, the central bore 264, the inflation port 260, and an appropriate connected pressurizing apparatus. A polycarbonate stop 280 aligns within the central bore 264 in the vicinity of the threaded portion 254, and includes a connection nipple 282 and a central lumen 284 through-which a guidewire can be passed. The Touhy Borst connector 255 applies pressure against an elastomeric gasket 257 and the silicone bumper to seal the Touhy Borst connector 255 to the central bore 264. A polyurethane tube 286 aligns over and is secured, such as by bonding glue 289 and 291, between connection nipples 282 and 277, thus connecting the polycarbonate stop 280 and the piston 276. A stainless steel wire braid 288 secures over and about the length of the polyurethane tube 286 by crimp rings 290 and 292, thus furthering the connection between the polycarbonate stop 280 and the piston 276.

Figure 15:
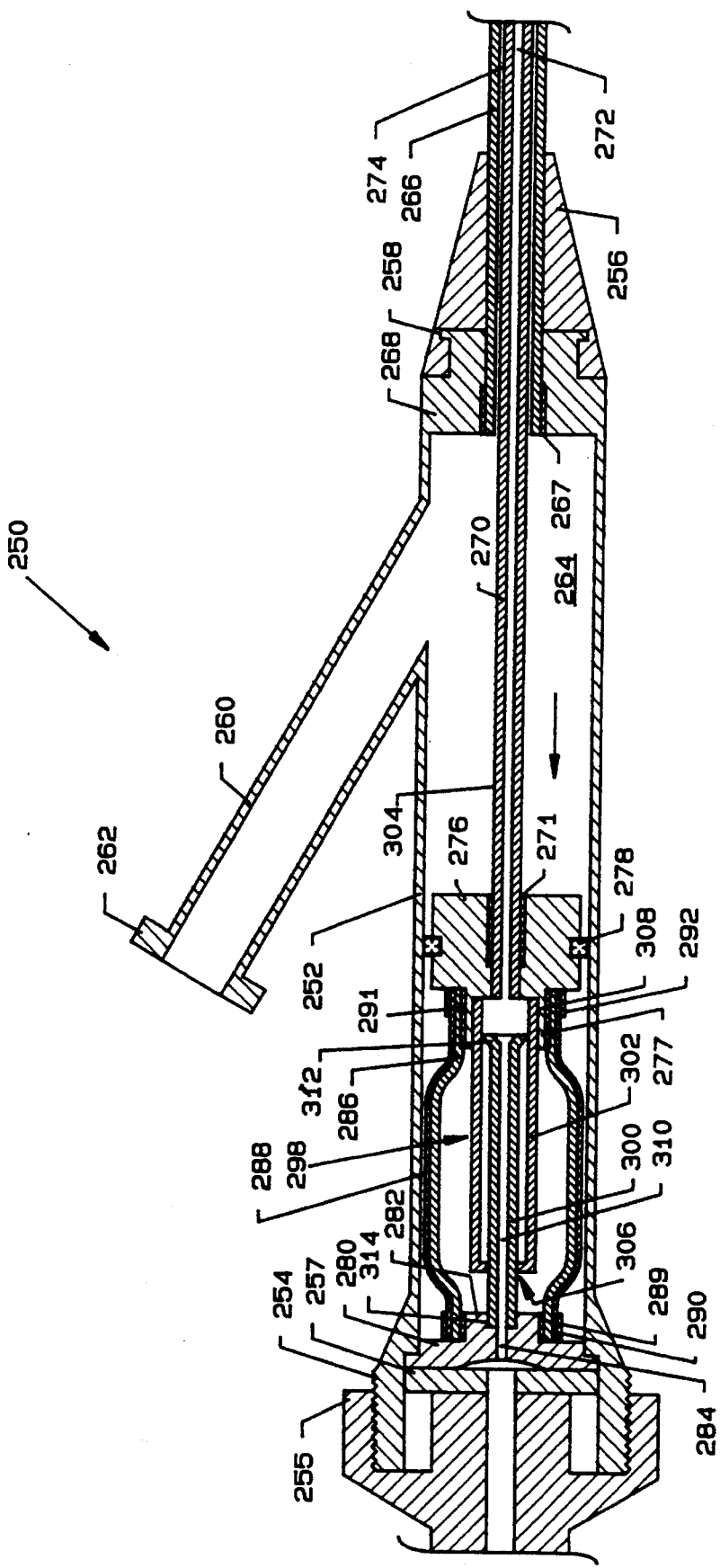

A tubular telescoping assembly 298 comprised of an inner telescoping tube 300 and an outer telescoping tube 302 aligns and secures between the polycarbonate stop 280 and the piston 276. The outer telescoping tube 302 including a lumen 304 and an orifice 306 at the end of lumen 304 is press fit into a cavity 308 in the nipple 277. Correspondingly, the inner telescoping tube 300 having a lumen 310 and a flared seal member 312 is press fit into a cavity 314 in the end of nipple 282 of the silicone bumper 280. The inner telescoping tube 300 slidingly engages orifice 306 of the outer telescoping tube 302. The tubular telescoping assembly 298 offers guidance for a guide wire aligned through the central bore 284 of the polycarbonate stop 280 for ease of alignment with lumen 272 of the polyimide tube 270. A flared seal member 312 is tapered inwardly to intersect with lumen 310. The flared seal member 312 having an inwardly tapered surface 313 assists in guidance of a front loaded guide wire inserted in the distal end of lumen 272 and moved proximally through lumen 304, 310, 284 gasket 257 and through the Touhy Borst connector 255. The tubular telescoping assembly 298 also stabilizes the polyurethane tube 286 when the piston 276 is positioned as illustrated in FIG. 15. Curling or kinking or other misalignment of the polyurethane tube 286 and of the stainless steel wire braid 288 is eliminated as the tubular telescoping assembly 298 acts as a horizontal guide along the length of the central bore 264.

MODE OF OPERATION OF THE THIRD ALTERNATIVE EMBODIMENT

FIG. 15 illustrates the mode of operation of the hub 250 in conjunction with a balloon catheter, including a balloon of extended length, such as a length of up to 12 cm. A pressurized saline solution applied to the inflation port 260 flows through the lumen 274 of the flexible polymer tube 266 to inflate an extended length balloon at the distal end of the balloon catheter. As the balloon is inflated, the polyimide tube 270 is forced to retract proximally partly by the shortening of the expanding balloon which develops a shorter length during inflation, thus driving the polyimide tube 270 proximally, and partly by the pressurized saline force driving the piston 276 proximally. The driving of the piston 276 proximally cause several occurrences. Firstly, the polyurethane tube 286 and the stainless steel wire braid 288 are compressed along their common axis along their length as the piston is driven proximally. This compression applied to the ends of the polyurethane tube 286 and the stainless steel wire braid 288, causes the ends to expand from their position of memory concentrically and outwardly about their common axis, and also to be compressed to a shorter longitudinal dimension. Energy is stored during the compression process, and is held in readiness by the pressure exerted by the saline pressurizing medium. Secondly, air captured in the central bore 264 between the piston 276 and the polycarbonate stop 280 is compressed as the piston 276 is forced proximally and is also held in readiness. Thus, energy is stored by the compressed polyurethane tube 286, the surrounding compressed stainless steel wire braid 288, and also by compressed air in the portion of the central bore proximal to the piston 276. During compression the outer telescoping tube 302 is driven proximally along the inner telescoping tube 300.

When it is desired to collapse and retract the balloon at the distal end of a balloon catheter, pressure to the inflation port 260 is released thereby releasing stored energies and causing the polyimide tube 270 to be driven distally to enable full and proper balloon collapsing. This enablement is caused by the stored energy being released. The compression energy of the compressed polyurethane tube 286 and the stainless steel wire braid 288 returning to their memory positions caused the polyimide tube 270 to be driven distally. The compression energy stored by the compressed air proximal to the piston 276 also aids in movement of the polyimide tube 270 distally to also assist in collapsing of the balloon.

Various modifications can be made to the present invention without departing from the apparent scope hereof.

We claim:

1. A balloon catheter comprising:
   a. a balloon assembly;
   b. means, connected to said balloon, to inflate and deflate said balloon assembly;
   c. a hub including a central tubular member with proximal and distal ends, and a flexible polymer tube aligned and secured through said distal end of said hub, said flexible polymer tube having an interior lumen and being communicatively connected to said balloon assembly;
   d. a central tube including an interior lumen, said tube being communicatively connected to said balloon, slidably aligned in said lumen of said flexible polymer tube, and having a proximal end extending into said hub central tubular member;
   e. a piston slidably, sealably disposed in said hub central tubular member and secured to said central tube distal end and,
   f. a polymer stop disposed at said proximal end of said hub defining a sealed air space in said hub between said piston, said air space being compressed during inflation to aid in balloon assembly inflation and deflation.

2. The catheter of claim 1 including a tubular telescoping assembly of:
   a. an inner telescoping tube and an outer telescoping tube between said piston and said stop;
   b. said outer telescoping tube including a lumen and an orifice engaged into a cavity in a nipple of said piston; and,
   c. said inner telescoping tube engages into an orifice of said outer telescoping tube whereby said telescoping assembly provides for guidance of a guidewire.

3. The catheter of claim 2 including a flared seal in said inner telescoping tube.

4. The catheter of claim 3 wherein said flared seal is tapered inwardly.

5. The catheter of claim 2 including a wire braid between said piston and said nipple.

6. The catheter of claim 5 wherein said braid is a re-enforcing non-compliant material such as stainless steel.

7. The catheter of claim 1 wherein said balloon means can be up to 12 cm in length.

8. The catheter of claim 1 wherein said central tubular means includes an inflation port.

9. The catheter of claim 1 wherein said central tubular means tube is a polymer such as polyimide.

10. The catheter of claim 1 wherein said stop is a polymer such as polycarbonate.

11. The catheter of claim 1 further comprising a ring disposed about said piston.

12. A balloon catheter comprising:
    a. a balloon means;
    b. an inflation means connected to said balloon means;
    c. a hub means including a central tubular member with a threaded proximal end and a distal end with a flexible conical tip, and a flexible polymer tube aligned and secured through said distal end of said hub, said flexible polymer tube having a lumen and being communicatively connected to said balloon means;
    d. a tube including a lumen adapted to receive an inserted guidewire, said tube being slidably aligned in said lumen of said flexible polymer tube;
    e. a piston disposed in said hub and secured to said tube, and having ring means for creating a pressure seal between said piston and said hub;
    f. a polycarbonate stop at said proximal end of said hub, and
    g. a tubular telescoping assembly, including an inner telescoping tube and an outer tube between said piston and said stop, said outer tube including a lumen and an orifice engaged into a cavity in a nipple of said piston, and said inner telescoping tube engaging into an orifice of said outer tube whereby said telescoping assembly guides an inserted guidewire.

13. The catheter of claim 12 including a flared seal in said inner telescoping tube.

14. The catheter of claim 13 wherein said flared seal is tapered inwardly.

15. The catheter of claim 12 including a wire braid between said piston and said nipple.

16. The catheter of claim 12 wherein said balloon means can be up to 12 cm in length.

17. A hub comprising:
   a. a central tubular member with a proximal threaded end for connection to a connector and a distal end with a flexible conical tip and a flexible polymer tube aligned and secured therethrough;
   b. a tube including a guidewire lumen, said tube being slidably aligned in a lumen of said flexible polymer tube;
   c. a piston in said central tubular member and secured to said tube, and having sealing ring means for creating a pressure seal between said piston and said central tubular member;
   d. a polymer stop at said proximal end of said central tubular member; and
   a telescoping tube assembly including an inner tube being connected at one end to said stop, and an outer tube being connected at one end to said piston, said inner and outer tubes being telescopingly arranged with respect to each other.

* * * * *